United States Patent [19]
Norris

[11] Patent Number: 6,114,531
[45] Date of Patent: Sep. 5, 2000

[54] PROCESS FOR PREPARING QUINOLONE AND NAPHTHYRIDONE CARBOXYLIC ACIDS

[75] Inventor: Timothy Norris, Gales Ferry, Conn.

[73] Assignee: Pfizer Inc., New York, N.Y.

[21] Appl. No.: 09/324,385

[22] Filed: Jun. 2, 1999

Related U.S. Application Data

[60] Provisional application No. 60/094,440, Jul. 28, 1998.

[51] Int. Cl.[7] .................... A61K 31/47; C07D 215/16; C07D 215/20; C07D 215/36
[52] U.S. Cl. ............................. 546/156; 514/312
[58] Field of Search ............... 546/156; 514/312

[56] References Cited

PUBLICATIONS

Casreact 127:248005, 1997, Glushkov.
Casreact 125:247630, 1995, Palomo.
Casreact 124:343143, Busch, 1996.
Casreact 124:8852, Hommler, 1995.
CA 128:140606, Hawkins, 1998.
CA 126:264093, Allen, 1997.
CA 126:251417, Norris, 1997.
cA 119:117227, Brightly, 1992.

*Primary Examiner*—D. Margaret Seaman
*Attorney, Agent, or Firm*—Peter C. Richardson; Paul H. Ginsburg; Bryan C. Zielinski

[57] ABSTRACT

Antibacterial quinolone carboxylic acids and naphthyridone carboxylic acids, having an external amino group attached to their 7-substituent are prepared without the use, and subsequent removal, of blocking groups on the external amino group. In a preferred embodiment, the naphthyridone carboxylic acid is the antibiotic trovafloxacin.

6 Claims, No Drawings

PROCESS FOR PREPARING QUINOLONE AND NAPHTHYRIDONE CARBOXYLIC ACIDS

This application claims benefit of Provisional Application No. 60/094,440 filed Jul. 28, 1998.

1. FIELD OF THE INVENTION

This invention relates to a process for preparing antibacterial quinolone and naphthyridone carboxylic acids having an external, primary amino group. The process is performed without the use, or subsequent removal, of blocking groups on the external, primary amino group.

2. BACKGROUND OF THE INVENTION

Quinolone and naphthyridone carboxylic acids, zwitterionic salts thereof, and pharmaceutically acceptable salts thereof, are useful as antibacterial agents, and have been prepared according to methods described in, e.g., U.S. Pat. No. 4,738,968 to Matsumoto et al., U.S. Pat. No. 4,382,937 to Matsumoto et al., U.S. Pat. No. 4,382,892 to Hayakawa et al., U.S. Pat. No. 4,571,396 to Hutt et al., U.S. Pat. No. 4,416,884 to Ishikawa et al., U.S. Pat. No. 4,775,668 to Jefson et al., U.S. Pat. No. 5,164,402 to Brighty and U.K. Patent Publication No. 2,191,776 to Toyama Chemical Co. Ltd. Such quinolone and naphthyridone carboxylic acids, and zwitterionic salts thereof, have been obtained (see, e.g., U.S. Pat. No. 5,164,402 to Brighty) by coupling a compound of formula I

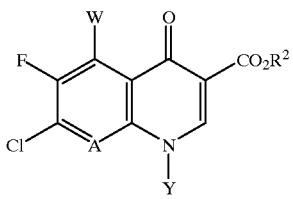

I wherein $R^2$ is $C_1$–$C_6$ alkyl, especially ethyl or methyl, or hydrogen; A is CH, CF, CCl, $COCH_3$, $CCH_3$, CCN or N; Y, when taken independently, is ethyl, t-butyl, vinyl, cyclopropyl, 2-fluoroethyl, p-fluorophenyl, or o,p-difluorophenyl; or A is a carbon atom and is taken together with Y and the carbon and nitrogen atoms to which A and Y are attached to form a five- or six-membered ring which may contain oxygen or a double bond, and which may have methyl or methylene attached to the ring; and W is H, F, Cl, Br, $C_1$–$C_4$ alkyl, $C_1$–$C_4$ alkoxy, amino or $NHCH_3$; with a cyclic compound having an amino group, and having the formula II $HR^1(CH_2)_aNHX$    II wherein a is 0 or 1; $R^1$ is a cyclic secondary amino group; and X is a protecting group, such as tertiary-butoxycarbonylamino.

The coupling of a compound of formula I with a compound of formula II results in the displacement of the chloro group from, and the attachment of the secondary amino group to, the 7-carbon atom of the compound of formula I. Examples of compounds of formula II are 3-azabicyclo[3.1.0]hexane and 3-azabicyclo[4.1.0]heptane (U.S. Pat. No. 5,164,402 to Brighty), and pyrrolidines (U.S. Pat. No. 4,382,937 and U.S. Pat. No. 4,738,968 to Matsumoto et al.), each bearing a protected amino group.

It is necessary that a compound of formula II have a protecting group (in the form of "X") on its primary amino group to prevent the otherwise unprotected primary amino group from competing with the secondary amino group for bond formation with the 7-carbon atom of the compound of formula I. However, the need for such a protecting group adds at least two extra steps to the synthesis of quinolone and naphthyridone carboxylic acids: (1) the addition of the protecting group onto the primary amino group of a compound of formula II prior to reaction with a compound of formula I, and (2) the removal of the protecting group subsequent to reaction with a compound of formula I. These additional steps naturally add to the cost of the synthesis, lengthen the time in which the synthesis can be completed, and limit the time that workers can spend performing other experiments. Accordingly, a process for obtaining quinolone and naphthyridone carboxylic acids that omits the use of protecting groups would be highly desirable and advantageous.

Citation or identification of any reference in Section 2 of this application shall not be construed as an admission that such reference is available as prior art to the present application.

3. SUMMARY OF THE INVENTION

According to the invention, a process is provided for the preparation of a compound of formula III:

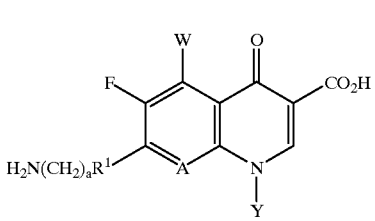

III or a zwitterionic salt thereof, comprising the step of contacting, in the presence of a tertiary amine base:

(a) a compound of formula IV:

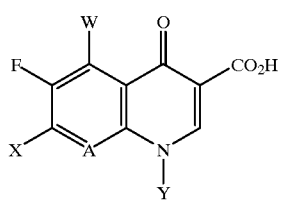

IV wherein

A is CH, CF, CCl, $COCH_3$, $CCH_3$, CCN or N;

Y, when taken independently, is ethyl, t-butyl, vinyl, cyclopropyl, 2-fluoroethyl, p-fluorophenyl, or o,p-difluorophenyl;

or A is carbon atom and is taken together with Y and with the carbon and nitrogen atoms to which A and Y are attached to form a five- or six-membered ring which may contain oxygen or a double bond, and which may have methyl or methylene attached to the ring;

W is H, F, Cl, Br, C1–C4 alkyl, C1–C4 alkoxy, amino or NHCH3; and

X is halogen, with (b) a compound of formula V:

$HR^1(CH_2)_aNH_2 \cdot (ZH)_b$      V wherein $R^1$ is a cyclic secondary amino group having a nucleophilic nitrogen atom;

ZH is an acid;

a is 0 or 1; and b ranges from 1 to the number of basic nitrogen atoms in the compound of formula V.

In a preferred embodiment of the invention, the compound of formula IV is 7-chloro-1-(2,4-difluorophenyl)-6-fluoro-1,4-dihydro-4-oxo-1,8-naphthyridine-3-carboxylic acid:

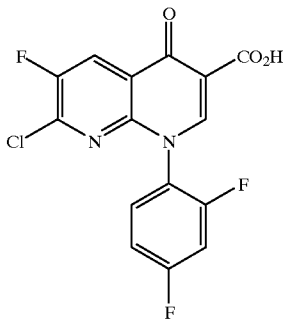

the compound of formula V is a diacid salt of (1α, 5α, 6α)-6-amino-3-azabicyclo[3.1.0.]hexane and having the formula VI:

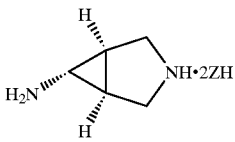
     VI and the compound of formula III is (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid, also known as trovafloxacin:

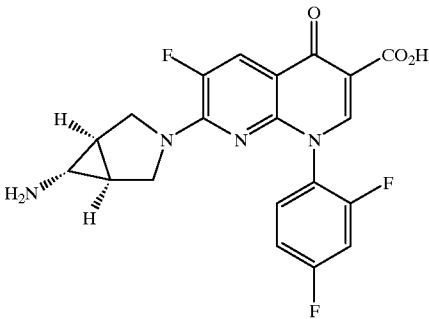

4. DETAILED DESCRIPTION OF THE INVENTION

4.1 Definitions

The term "alkyl" as used herein includes a straight or branched chain hydrocarbyl group such as methyl, ethyl, propyl, iso-propyl, n-butyl, iso-butyl, sec-butyl, tert-butyl, etc.

The term "aryl" as used herein includes an aromatic hydrocarbyl group, such as phenyl or naphthyl, optionally substituted with 1 to 3 substituents independently selected from the group consisting of fluoro, chloro, cyano, nitro, trifluoromethyl, $(C_1-C_6)$alkoxy, $(C_6-C_{10})$aryloxy, trifluoromethoxy, difluoromethoxy and $(C_1-C_6)$alkyl.

The term "basic nitrogen atoms" as used herein means nitrogen atoms of a compound of formula V that are capable of forming a salt with ZH.

The term "coupling reaction" as used herein means a reaction between a compound of formula IV and a compound of formula V to afford a compound of formula III, or a zwitterionic salt thereof.

The term "cyclic secondary amino group" as used herein means a mono-, bi- or tricyclic alkyl or alkenyl group having, within at least one ring thereof, a nucleophilic nitrogen atom.

The term "halogen" as used herein means fluorine, chlorine, bromine and iodine.

The term "nucleophilic nitrogen atom" as used herein means a nitrogen atom forming three $sp^3$ bonds, one of which being with a hydrogen atom, and being capable of displacing a halogen atom from the 7-carbon atom of a compound of formula IV.

The term "tertiary amine base" as used herein means an organic compound having a nitrogen atom forming three bonds, each of which being an $sp^2$ or $sp^3$ bond, solely with carbon atoms.

The term "zwitterionic salt thereof" of formula III, as used herein, means a compound of formula III wherein its carboxylic acid proton resides on any one of its nitrogen atoms, existing in the form of an internal salt.

4.2 Compounds of Formula IV

The compounds of formula IV can be obtained by hydrolysis of the simple esters of compounds of formula IV which in turn may be prepared according to the methods of U.S. Pat. No. 4,738,968 to Matsumoto et al., U.S. Pat. No. 4,382,892 to Hayakawa et al., U.S. Pat. No. 4,416,884 to Ishikawa et al., or United Kingdom Patent Publication No. GB 2,191,776 to Toyama Chemical Co. Ltd.

Alternatively, the compounds of formula IV, wherein A is N, and W, X and Y are defined above, can be prepared according to Scheme 1, below:

Nicotinic acid 1 is converted to its acid chloride derivative and then condensed with ethyl acetoacetate to afford ester 2a. Deacetylation of 2a with pyridinium tosylate affords β-ketoester 2b which can be obtained directly from the acid chloride derivative of 1 upon condensation with ethyl malonate in the presence of butyllithium. Treatment of 2b with triethylorthoformate and acetic anhydride provides enol ethers 3 which undergo an addition-elimination reaction with an amine HN—Y to provide enamines 4. Cyclization of 4 is effected using a base such as sodium carbonate or sodium hydride to afford naphthyridone carboxylic acid ester 5 which is hydrolyzed using methanesulfonic acid in 9:1 tetrahydrofuran/water to provide naphthyridone carboxylic acid 6, a compound of formula IV.

Scheme

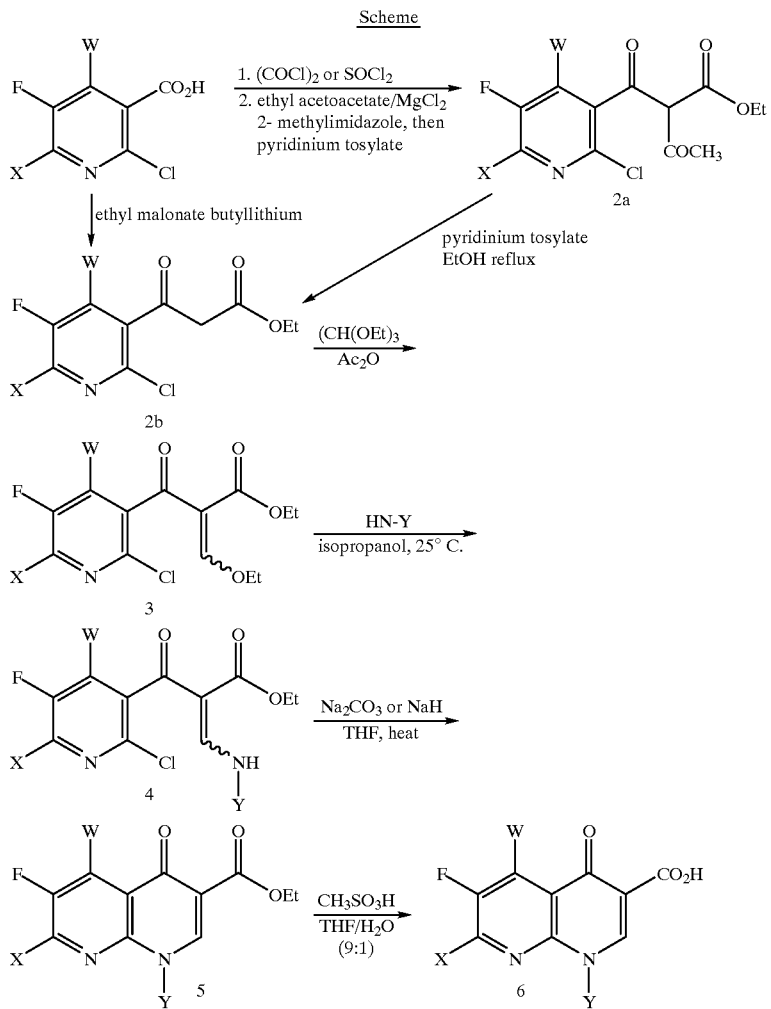

Preferably, X is chloro. More preferably, Y is 2,4-difluorophenyl or cyclopropyl, W is hydrogen, X is chloro and A is N or CH. Most preferably, Y is 2,4-difluorophenyl, W is hydrogen, X is chloro and A is nitrogen.

Most preferably, the compound of formula IV is 7-chloro-1-(2,4-difluorophenyl)-6-fluoro-1,4-dihydro-4-oxo-1,8-naphthyridine-3-carboxylic acid, which is prepared by hydrolyzing, preferably with methanesulfonic acid and 9:1 tetrahydrofuran:water, ethyl 7-chloro-1-(2,4-difluorophenyl)-6-fluoro-1,4-dihydro-4-oxo-1,8-naphthyridine-3-carboxylate. Ethyl 7-chloro-1-(2,4-difluorophenyl)-6-fluoro-1,4-dihydro-4-oxo-1,8-naphthyridine-3-carboxylate can be prepared according to United Kingdom Patent Publication No. GB 2,191,766 to Toyama Chemical Co. Ltd.

4.3 Compounds of Formula V

The compounds of formula V are represented by the formula:

wherein $R^1$ is a cyclic secondary amino group, a is 0 or 1, ZH is an acid, and b ranges from 1 to the number of basic nitrogen atoms in the compound of formula V.

Useful cyclic secondary amino groups include, but are not limited to, aziridinyl, azetidinyl, pyrrolidinyl, 3-hydroxylpyrrolidinyl, 3-dimethylaminopyrrolidinyl, 3-acetylaminopyrrolidinyl, 3-methylacetylaminopyrrolidinyl, 3-aminopyrrolidinyl, 3-methylaminopyrrolidinyl, piperidinyl, 4-methylaminopiperidinyl, piperazinyl, N-methylpiperazinyl, N-ethylpiperazinyl, N-propylpiperazinyl, N-isopropylpiperazinyl, N-acetylpiperazinyl, 3-methylpiperazinyl, N-methyl-2-methylpiperazinyl, N-methyl-3-methylpiperazinyl, N-allylpiperazinyl, N-ethoxycarbonyl-2-methylpiperazinyl, 3,5-dimethylpiperazinyl, 2,5-dimethylpiperazinyl, N-(hydroxyethyl)piperazinyl, morpholinyl, hexamethyleneiminyl, heptamethyleneiminyl, 3-azabicyclo[3.1.0]hexyl and 3-azabicyclo[4.1.0]heptyl groups, the cyclic secondary amino groups being optionally substituted with one or more nitro, chloro, bromo, fluoro, iodo or alkylsulfonyl groups. Examples of optionally substituted 3-azabicyclo[3.1.0]hexyl and 3-azabicyclo[4.1.0]heptyl groups are found in U.S. Pat. No. 5,164,402 to Brighty.

The compounds of formula V are salts of $HR^1(CH_2)_aNH_2$ and ZH. Any carboxylic acid is suitable as ZH; preferably, ZH is a mineral acid such as HCl, HBr, nitric acid or sulfuric acid; a $C_1$–$C_6$ alkylsulfonic acid such as methanesulfonic acid, trifluoromethanesulfonic acid or ethanesulfonic acid; or a $C_6$–$C_{10}$ arylsulfonic acid such as benzenesulfonic acid, toluenesulfonic acid or naphthalenesulfonic acid.

In general, the compounds of formula V are obtained by admixing, in any suitable organic solvent, ZH and $HR^1(CH_2)_aNH_2$, wherein from one equivalent of ZH, or a slight excess thereof, is used per equivalent of $HR^1(CH_2)_aNH_2$, up to one equivalent of ZH, or a slight excess thereof, per equivalent of basic nitrogen atom in $HR^1(CH_2)_aNH_2$. The solvent may be removed via conventional means to provide the compound of formula V or the solution may be used for further reaction according to the invention. It will be understood that because $R^1$ is a cyclic secondary amino group, $HR^1(CH_2)_aNH_2$ has at least two basic nitrogen atoms, i.e., —$NH_2$ and the secondary amino group(s) of $R^1$; accordingly, "b," the preferred number of ZH units in the compound of formula V, is at least two. Alternatively, where the precursor of $HR^1(CH_2)_aNH_2$ is a compound that has an acid-labile protecting group on —$NH_2$ and on the secondary amino group (see U.S. Pat. No. 5,164,402 to Brighty), the compound of formula IV may be formed in situ by removal of the protecting groups with ZH.

In one embodiment of the invention, $HR^1(CH_2)_aNH_2$ is 3-aminopyrrolidine or 3-aminethylpyrrolidine. In another embodiment of the invention, $R^1$ is a bicyclic group that comprises a 3-membered ring and a 4-membered ring. Examples of such bicyclic groups are found in U.S. Pat. No. 5,164,402 to Brighty.

In a preferred embodiment of the invention, b is the numner of basic nitrogens in the compound of formula V.

Preferably, $HR^1(CH_2)_aNH_2$ is (1α, 5α, 6α)-6-amino-3-azabicyclo[3.1.0.]hexane. Most preferably, the compound of formula V is the ditosylate salt of (1α, 5α, 6α)-6-amino-3-azabicyclo[3.1.0.]hexane.

4.4 Compounds of Formula III

The compounds of formula III have the structure:

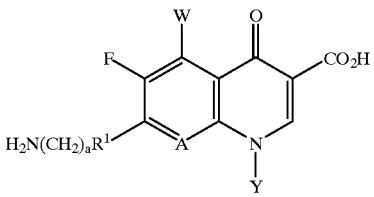

and include zwitterionic salts thereof.

Compounds of formula III, and zwitterionic salts thereof, are prepared by a process comprising the step of contacting, in the presence of a tertiary amine base:

(a) a compound of formula IV:

IV

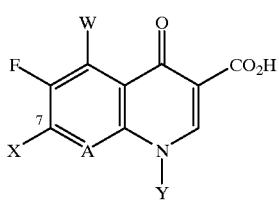

wherein

A is CH, CF, CCl, $COCH_3$, $CCH_3$, CCN or N;

Y, when taken independently, is ethyl, t-butyl, vinyl, cyclopropyl, 2-fluoroethyl, p-fluorophenyl, or o,p-difluorophenyl;

or A is carbon atom and is taken together with Y and with the carbon and nitrogen atoms to which A and Y are attached to form a five- or six-membered ring which may contain oxygen or a double bond, and which may have methyl or methylene attached to the ring;

W is H, F, Cl, Br, C1–C4 alkyl, C1–C4 alkoxy, amino or NHCH3; and

X is halogen, with (b) a an interger ranging from 1 to compound of formula V:

$$HR^1(CH_2)_aNH_2 \cdot (ZH)_b \qquad V$$

wherein $R^1$ is a cyclic secondary amino group having a nucleophilic nitrogen atom;

ZH is an acid;

a is 0 or 1; and b ranges from one to the number of basic nitrogen atoms in the compound of formula V.

The coupling reaction proceeds in good yield, e.g., 75% yield or greater, and avoids the use, i.e., addition and removal, of protecting groups.

Without being bound by any particular theory, Applicant believes that the nucleophilic nitrogen atom of the secondary amino group of the compound of formula V displaces the halogen group (X) from the 7-carbon atom of the compound of formula IV, and forms a bond therewith. It will be understood that since the coupling reaction is performed in the presence of a tertiary amine base, protonated forms of the compound of formula IV will exist in some equilibrium concentration with the protonated form of the tertiary amine base. It is believed that protonation of the —$NH_2$ group of the compound of formula V renders the —$NH_2$ group non-nucleophilic, so that the resulting —$NH_3^+$ group does not compete effectively with the cyclic secondary amino group of the compound of formula V for the 7-carbon atom of the compound of formula IV. Following addition of the cyclic secondary amino group and departure of $X^-$, the resulting compound of formula III can spontaneously form a stable internal salt in the form of a zwitterion and, depending upon the presence or type of coupling reaction solvent, precipitate from solution.

In general, compounds of formula III or zwitterionic salts thereof are obtained by combining, in no preferred order, a compound of formula IV, a compound of formula V, and a tertiary amine base.

Preferably, the tertiary amine base has the formula $(R^2)(R^2)(R^2)N$, wherein each $R^2$ is independently a $C_1$–$C_6$ alkyl or $(C_6$–$C_{10})$aryl group; or the tertiary amine base is an aromatic compound having an endocyclic nitrogen atom. Suitable tertiary amine bases include, but are not limited to, triethylamine, N,N-diisopropylethylamine, dimethylisopropylamine, methyldibutylamine, triphenylamine, pyridine, 4-dimethylaminopyridine, 2,6-lutidine, 2,4,6-collidine, N,N,N',N'-tetramethyl-1,8-naphthalenediamine, and the like.

The ratio of the compound of formula IV to the compound of formula V is generally about 1:1, although a slight excess of either the compound of formula IV or the compound of formula V may be used. The ratio of the tertiary amine base to the compound of formula IV or to compound of formula V is generally from about 1:1 to about 10:1, preferably from about 2:1 to about 5:1, and most preferably about 3:1.

The use of the tertiary amine base substantially avoids the formation of an unwanted byproduct of the coupling reaction, i.e., the product formed from the reaction of both the secondary and primary amino groups of a compound of formula V with the halogen groups (X) at the 7-carbon atom of at least one and, preferably, at least two equivalents of a compound of formula IV. For example, the use of triethylamine in the coupling reaction between 7-chloro-1-(2,4-difluorophenyl)-6-fluoro-1,4-dihydro-4-oxo-1,8-naphthyridine-3-carboxylic acid and the ditosylate salt of (1α, 5α, 6α)-6-amino-3-azabicyclo[3.1.0]hexane greatly reduces the formation of the compound of the formula VII:

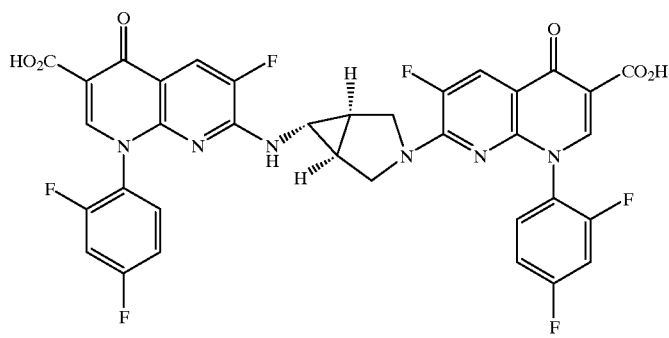

VII

In addition, when triethylamine is used in the coupling reaction between 7-chloro-1-(2,4-difluorophenyl)6-fluoro-1,4-dihydro-4-oxo-1,8-naphthyridine-3-carboxylic acid and the ditosylate salt of (1α, 5α, 6α)-6-amino-3-azabicyclo [3.1.0]hexane, the formation of hypothetical compound VIII cannot be detected:

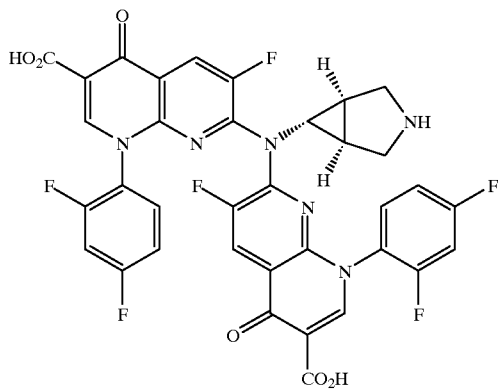

VIII

Suitable coupling reaction solvents include ($C_1$–$C_6$) alcohols, such as methanol, ethanol and isopropanol; ethers, such as tetrahydrofuran (THF) and diethylether; polar aprotic solvents, such as dimethylsulfoxide, acetonitrile, dimethylformamide and N-methylpyrrolidinone; and mixtures thereof. The compounds of formula IV and formula V should be at least partially soluble in the coupling reaction solvent chosen; accordingly, it is well within the purview of one of skill in the art to select an appropriate solvent or mixture of solvents. Preferably, the coupling reaction solvent is methanol or ethanol. More preferably, the coupling reaction solvent is methanol.

The coupling reaction is conveniently performed at a temperature of about 60° C. or above, and for a period of time ranging from about 1 hour to about 48 hours, preferably for a period of time ranging from about 2 hours to about 24 hours. More preferably, the coupling reaction is performed at the reflux temperature of the particular solvent used, and for a period of time ranging from about 6 hours to about 20 hours.

Generally, the product of the coupling reaction, i.e., a compound of formula III or a zwitterionic salt thereof, is insoluble in the coupling reaction solvent, and precipitates upon formation. Accordingly, the compound of formula III or zwitterionic salt thereof can be isolated by merely filtering it from the coupling reaction solvent, and optionally washing it with the same type of coupling reaction solvent. In the case where the compound of formula III or zwitterionic salt thereof is soluble in the coupling reaction solvent, the compound of formula III or zwitterionic salt thereof can be isolated by concentrating the coupling reaction mixture, optionally in vacuo, and purifying the resulting residue using column, e.g., silica gel, chromatography; crystallization from common laboratory solvents; or another purification method known to those skilled in the art.

Preferably, the compound of formula III is trovafloxacin, which can exist in the form of its zwitterionic salt. Trovafloxacin is conveniently prepared by contacting, in the presence of a tertiary amine base described above, 7-chloro-1-(2,4-difluorophenyl)-6-fluoro-1,4-dihydro-4-oxo-1,8-naphthyridine-3-carboxylic acid with a compound of formula VI. Preferably, the compound of formula VI is the ditosylate salt of (1α, 5α, 6α)-6-amino-3-azabicyclo[3.1.0] hexane, and the tertiary amine base is triethylamine.

It is believed that the nucleophilic nitrogen atom of the secondary amino group of the compound of formula VI, i.e., the endocyclic nitrogen atom of (1α, 5α, 6α)-6-amino-3-azabicyclo[3.1.0]hexane, displaces the chloro group from the 7-carbon atom of 7-chloro-1-(2,4-difluorophenyl)-6-fluoro-1,4-dihydro-4-oxo-1,8-naphthyridine-3-carboxylic acid, and forms a bond therewith to provide trovafloxacin or a zwitterionic salt thereof.

Advantageously, the reaction of 7-chloro-1-(2,4-difluorophenyl)-6-fluoro-1,4-dihydro-4-oxo-1,8-naphthyridine-3-carboxylic acid with the compound of formula VI proceeds in the presence of a coupling reaction solvent described above. Preferably, the coupling reaction solvent is methanol.

4.6 Methods for Using Compounds of Formula III

The compounds of formula III, zwitterionic salts thereof and pharmaceutically acceptable salts thereof are useful for the treatment of bacterial infections of broad spectrum, particularly the treatment of gram-positive bacterial strains. Such pharmaceutically acceptable salts, including, but not limited to, hydrochloric, hydrobromic, methanesulfonic, tartaric, sulfuric, citric, acetic and maleic acid salts, are obtained by mixing one equivalent of the above acid with a compound of formula III, or with a zwitterionic salt thereof, in the presence of an inert solvent. The solvent can be concentrated to provide a pharmaceutically acceptable salt of a compound of formula III, or of a zwitterionic salt thereof, in isolated form.

The compounds of formula III, zwitterionic salts thereof and pharmaceutically acceptable salts thereof may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, the compounds can be administered intramuscularly or subcutaneously at dosage levels of about 0.1–50 mg/kg/day, advantageously 0.2–10 mg/kg/day given in a single daily dose or up to 3 divided doses.

The compounds of formula III, zwitterionic salts thereof and pharmaceutically acceptable salts thereof can be administered to humans for the treatment of bacterial diseases by either the oral or parenteral routes, and may be administered orally at dosage levels of about 0.1 to 500 mg/kg/day, advantageously 0.5–50 mg/kg/day given in a single dose or up to 3 divided doses. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of formula III, zwitterionic salts thereof and pharmaceutically acceptable salts thereof is shown by testing according to the Steer's replicator technique which is a standard in vitro bacterial testing method described by E. Steers et al., Antibiotics and Chemotherapy, 9, 307 (1959).

The following examples are set forth to assist in understanding the invention and should not, of course, be construed as specifically limiting the invention described and claimed herein. Such variations of the inventions which would be within the purview of those in the art, including the substitution of all equivalents now known or later developed, are to be considered to fall within the scope of the invention incorporated herein. In the examples below, unless otherwise indicated, "Ac" means acetyl, "Et" means ethyl, "Me" means methyl, and "THF" means tetrahydrofuran.

5. EXAMPLE
Synthesis of Trovafloxacin, an Illustrative Compound of Formula III

Example 1

(1α, 5α, 6α)-3-N-benzyl-6-nitro-2,4-dioxo-3-azabicyclo [3.1.0]hexane. N-Benzylmaleimide (500 g, 2.67 mole), 90% bromonitromethane (831 g, 5.34 mole), powdered molecular sieves, 200 mesh (2020 g) and toluene (12 dm$^3$) were stirred under nitrogen at −10° C. 1,2-dimethyl-1,4,5,6-tetrahydropyrimidine (616 g, 5.49 mole) was added slowly over about 3 hours maintaining the reaction temperature at <−8° C. throughout the addition. After completion of the addition, the reaction mixture was stirred for 1.5 hours at 25° C., filtered under a nitrogen atmosphere in a sealed pressure filter to remove sieves and resulting tar, and the sieves were washed with toluene (2 L). The combined filtrates were washed with 2N dilute hydrochloric acid (3×750 cm$^3$), treated with carbon (50 g) at 70° C., 1 hour filtered, concentrated, and triturated with 2-propanol (~4 dm$^3$) to obtain crystals of the above-titled product (223 g, 34%) mp 116–118° C.; (Found: C, 58.2; H, 4.1; N, 11.3. C$_{12}$H$_{10}$N$_2$O$_4$ requires C, 58.5; H, 4.1; N, 11.4%); m/z 246 (M+), 200 (M+ −NO$_2$, 100%); δH (300 MHz; CDCl$_3$) 7.3 (m, 5H, Ph), 4.54 (s, 2H, benzylic), 4.45 (s, 1H, 6b), 3.35 (s, 2H, 3-ring).

Example 2

(1α, 5α, 6α)-3-N-benzyl-6-nitro-3-azabicyclo[3.1.0] hexane. Tetrahydrofuran (350 cm$^3$), sodium borohydride (14.1 g) and (1α, 5α, 6α)-3-N-benzyl-6-nitro-2,4-dioxo-3-azabicyclo[3.1.0]hexane (35.0 g, mmol) obtained above were stirred under nitrogen for 0.25 hour and then treated dropwise with boron trifluoride THF complex containing 21.5% BF$_3$ (44.9 cm$^3$) so that the exotherm was controlled to <40° C. After addition was completed, the reaction mixture was stirred for 3 hours at 40° C., quenched slowly with water/THF 1:1 (70 cm$^3$) to avoid excessive foaming, and stirred for 0.5 hour at 50° C. to ensure that the quench of unreacted diborane generated in situ was completed. The quench formed a salt slurry which was filtered and washed with THF (140 cm$^3$); the combined filtrate was partially concentrated, diluted with water (350 cm$^3$) and further concentrated to remove most of the THF, and extracted with ethyl acetate (140 cm$^3$). The resulting ethyl acetate solution was concentrated to afford the above-titled product as a clear oil (30.6 g, 97%). Elemental analysis obtained from its mesylate salt, which was prepared by mixing an equivalent of (1α, 5α, 6α)-3-N-benzyl-6-nitro-3-azabicyclo[3.1.0] hexane with an equivalent of methanesulfonic acid in alcoholic solvent, and concentrating the resulting mixture (Found: C, 49.8; H, 6.0; N, 9.1; S, 10.2. C$_{12}$H$_{14}$N$_2$O$_2$.CH$_4$O$_3$S requires C, 49.7; H, 5.8; N, 8.9; S, 10.2%); m/z 218 (M+); δH (300 MHz; CDCl$_3$) 7.3 (m, 5H, Ph), 4.63 (s, 1H, 6b), 3.6 (s, 2H, benzylic), 3.14 (d, 2H, 5-ring), 2.51 (m, 2H, 3-ring).

Example 3

(1α, 5α, 6α)-3-N-benzyl-6-amino-3-azabicyclo[3.1.0] hexane. (1α, 5α, 6α)-3-N-benzyl-6-nitro-3-azabicyclo [3.1.0]hexane (25.05 g, 114.8 mmole), obtained above, 5% platinum on carbon catalyst, water content 66% (10.02 g), and methanol (250 cm$^3$) were hydrogenated in a Parr apparatus at 50° C., 3.5 atm, 24 hours. The catalyst was filtered off and the filtrate concentrated under vacuum to obtain the above-titled product as an oil (20.24 g, 93.6%), purity GC 81.5%. White crystals were obtained from hexane, mp 99–102° C. (hexanes). δH (300 MHz; CDCl$_3$) 7.31–7.18 (m, 5H), 3.53 (s, 2H), 2.94 (d, J=8.8 Hz, 2H), 2.64 (s, 1H), 2.36 (dm, J=8.6 Hz, 2H), 1.53 (s, 2H), 1.32 (dd, J=1.9 & 3.3 Hz); δC (75.5 MHz; CDCl$_3$) 139.5, 128.5, 128.1, 126.7, 59.2, 54.5, 32.5, 25.8; m/z 189 (M+H)+. Elemental analysis was obtained from its mesylate salt, which was prepared by mixing an equivalent of (1α, 5α, 6α)-3-N-benzyl-6-amino-3-azabicyclo[3.1.0]hexane with an equivalent of methanesulfonic acid in alcoholic solvent, and concentrating the resulting mixture (Found: C, 54.7; H, 7.1; N, 9.75; S, 11.5. $C_{12}H_{16}N_2 \cdot CH_4O_3S$ requires C, 54.9; H, 7.1; N, 9.85; S, 11.3%).

Example 4

(1α, 5α, 6α)-3-N-benzyl-6-tert-butyloxycarbonylamino-3-azabicyclo[3.1.0]hexane. Ethyl acetate (225 cm³), di-t-butyl dicarbonate (30.8 g, 141 mmol) and (1α, 5α, 6α)-3-N-benzyl-6-amino-3-azabicyclo[3.1.0]hexane (21.6 g, 115 mmol) obtained above were stirred at room temperature, and a solution of sodium carbonate (24.7 g, 233 mmol) and sodium hydroxide (9.35 g, 234 mmol) in water (200 cm³) was added at <30° C. The resulting two-phase reaction mixture was stirred for 3 hours at 30° C., and then separated. The resulting organic phase was concentrated to 25% of its original volume, and treated with hexane (150 cm³). The resulting crystals were isolated by filtration, and washed with hexane (50 cm³) to obtain the above-titled compound as white needles (18.4 g, 56%), mp 132–133° C. (EtOAc-hexane); (Found: C, 71.0; H, 8.45; N, 9.8. $C_{17}H_{24}N_2O_2$ requires C, 70.8; H, 8.4; N, 9.7%); m/z 289 (M+ +1); δH (300 MHz; CDCl₃) 7.29 (m, 5H, Ph), 4.62 (br s, NH), 3.61 (s, 2H benzylic), 3.1 (d, 2H, 5-ring), 2.92 (s, 1H, 6b), 2.50 (d, 2H, 5-ring), 1.56 (s, 2H, 3-ring), 1.4 (s, 9H), νmax (DRIFTS) cm⁻¹ 3370(NH), 1687 (urethane carbonyl).

Example 5

(1α, 5α, 6α)-6-tert-butyloxycarbonylamino-3-azabicyclo[3.1.0]hexane. Methanol (200 cm³), 10% palladium on charcoal catalyst containing 55% water (10 g) and (1α, 5α, 6α)-3-N-benzyl-6-tert-butyloxycarbonylamino-3-azabicyclo[3.1.0]hexane (20 g, 101 mmol) obtained above was hydrogenated on a Parr apparatus at room temperature overnight, and the catalyst was filtered off and washed with methanol (20 cm³). The combined filtrate was concentrated and displaced with cyclohexane (300 cm³). The resultant crystal slurry was further concentrated to about 100 cm³, and the product was isolated as the above-titled compound in the form of white crystals (12.2 g, 89%) mp 119–125° C. (cyclohexane); (Found: C, 60.35; H, 9.3; N, 14.1. $C_{10}H_{18}N_2O_2$ requires C, 60.6; H, 9.15; N, 14.1%); m/z 199 (M+ +1); δH (300 MHz; CDCl₃) 4.8 (br s, NH), 3.13 (d, 2H, 5-ring), 3.0 (s, NH), 2.9 (d, 2H, 5-ring), 2.29 (s, 1H, 6b), 1.57 (s, 2H, 3-ring), 1.39 (s, 9H), νmax(DRIFTS) cm⁻¹ 3321 (NH), 3174 (NH).

Example 6

Di-Tosylate Salt of (1α, 5α, 6α)-6-amino-3-azabicyclo[3.1.0]hexane. (1α, 5α, 6α)-6-tert-Butyloxycarbonylamino-3-azabicyclo[3.1.0]hexane (15.0 g, 75.8 mmol) obtained above, methanol (300 cm³) and toluenesulphonic acid (28.8 g, 151.6 mmol) were heated to reflux for 2 h. The reaction solution was concentrated to a crystal slurry, and the crystals isolated by filtration, washed with methanol and dried under vacuum to yield the above-titled compound (25.6 g, 76%), mp 247–248° C. (methanol); (Found: C, 51.5; H, 6.0; N, 6.3; S, 14.55. $C_5H_{10}N_2 \cdot C_{14}H_{16}O_6S_2$ requires C, 51.8; H, 5.9; N, 6.3; S, 14.5%); m/z 96 (M+ −2); δH (400 MHz; d6-DMSO) 8.49 (br s, 5H, NH and SO₃H), 7.51 (d, 2H, Abq), 7.12 (d, 2H, Abq), 3.3 (m, 4H, 5-ring), 2.6 (s, 1H, 6b), 2.27 (s, 6H, ArMe), 2.11 (s, 2H, 3-ring).

Example 7

7-Chloro-1-(2,4-difluorophenyl)-6-fluoro-1,4-dihydro-4-oxo-1,8-naphthyridine-3-carboxylic acid. A mixture of tetrahydrofuran (450 cm³), water (50 cm³), methanesulfonic acid (127 cm³) and ethyl 7-chloro-1-(2,4-difluorophenyl)-6-fluoro-1,4-dihydro-4-oxo-1,8-naphthyridine-3-carboxylate (United Kingdom Patent Publication No. GB 2,191,776) was heated at reflux for 1 hour, and then cooled to 25° C. The resulting crystals were isolated, washed with tetrahydrofuran, and dried under vacuum to afford 41.3 g (89%) of the above-titled compound: m.p.=250° C.; (Found: C, 50.4; H, 1.7; Cl, 9.9; F, 16.0; N, 8.0. $C_{15}H_6ClF_3N_2O_3$ requires C, 50.8; H, 1.7; Cl, 10.0; F, 16.1; N, 7.9%); ¹H NMR (300 MHz, d₆-DMSO) δ 13.9 (s, 1H), 9.09 (s, 1H), 8.77 (d, J=7.5 Hz, 1H), 7.86 (td, J=5.9 and 8.8 Hz, 1H), 7.66 (ddd, J=2.7, 9.0 and 11.8 Hz, 1H), 7.39 (tm, J=8.6 Hz, 1H), 7.39 (tm, J=8.6 Hz, 1H); νmax (DRIFTS) cm⁻¹ 3130, 3060, 2947, 2885, 2821, 2723, 2637, 2594, 1734, 1641, 1623, 1579, 1544, 1516.

Example 8

Trovafloxacin 7-Chloro-1-(2,4-difluorophenyl)-6-fluoro-1,4-dihydro-4-oxo-1,8-naphthyridine-3-carboxylic acid (500 mg, 1.41 mmol) obtained above, the di-tosylate salt of (1α, 5α, 6α)-6-amino-3-azabicyclo[3.1.0]hexane (624 mg, 1.41 mmol) obtained above, triethylamine (0.6 cm³, 4.23 mmol) and methanol (5 cm³) were refluxed for 16 hours. The resulting white solid was collected by filtration, refluxed in THF and re-isolated to give the title product as its zwitterion (450 mg, 75%), m.p. 225–228° C. (decomp.). δ H (300 MHz; d₆-DMSO): 8.81 (s,1 H), 8.03 (d, J=12.7 Hz, 1H), 7.80 (td, J=6.0 and 8.7 Hz), 7.63(m, 1H), 7.35(tm, J=8.6 Hz, 1H), 3.2–3.8(br.m, 4H), 1.92(s, 1H), 1.53 (s, 2H).

The compound of formula VII was isolated from the mother liquor by chromatography. δ H (300 MHz; d₆-DMSO)14.85(bs, 2H), 2.85 (s, 1H), 8.80(s, 1H); 8.56 (bs, 1H, 8.07 (d, J=5.7 Hz, 1H), 8.04 (d, J=3.6 Hz, 1H), 7.84–7.82 (m, 2H), 7.64 (td, J=9.7 and 2.5 Hz, 1H), 7.40–7.36 (m, 2H), 7.25 (bs, 1H), 3.50 (bs, 4H), 2.14 (s, 1H), 1.87 (bs, 2H).

A number of references have been cited, the entire disclosures of which are incorporated herein by reference.

What is claimed is:

1. A process for preparing trovafloxacin:

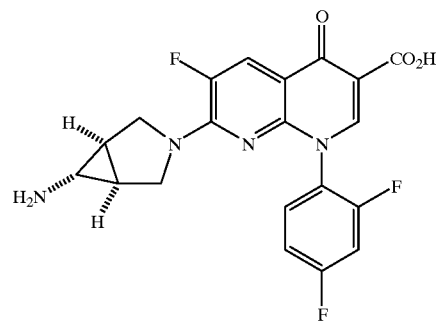

or a zwitterionic salt thereof, comprising the step of contacting, in the presence of a tertiary amine base:

(a) 7-chloro-1-(2,4-difluorophenyl)-6-fluoro-1,4-dihydro-4-oxo-1,8-naphthyridine-3-carboxylic acid, with (b) a compound of formula VI:

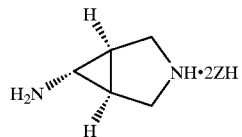

VI wherein ZH is an acid.

2. The process according to claim 1, wherein the acid is selected from the group consisting of a mineral acid, a $C_1-C_6$ alkylsulfonic acid and a $C_6-C_{10}$ arylsulfonic acid.

3. The process according to claim 2, wherein the $C_6-C_{10}$ arylsulfonic acid is toluenesulfonic acid.

4. The process according to claim 1, wherein the process is performed in the presence of an organic solvent.

5. The process according to claim 4, wherein the organic solvent is methanol.

6. The process according to claim 1, wherein the tertiary amine base is triethylamine.

* * * * *